United States Patent
Anderson et al.

(10) Patent No.: US 6,262,287 B1
(45) Date of Patent: Jul. 17, 2001

(54) FRAGRANCE PRECURSOR COMPOUNDS

(75) Inventors: Denise Anderson, Zürich; Georg Frater, Winterthur, both of (CH)

(73) Assignee: Givaudan-Roure (International) SA, Vernier-Geneve (CH)

( * ) Notice: Subject to any disclaimer, the term of this patent is extended or adjusted under 35 U.S.C. 154(b) by 0 days.

(21) Appl. No.: 09/076,519

(22) Filed: May 12, 1998

(30) Foreign Application Priority Data

May 15, 1997 (EP) .................................................. 97107970

(51) Int. Cl.$^7$ .............................. C07F 7/21; C07F 7/08; C08G 77/38; A61K 7/32

(52) U.S. Cl. .................... 556/437; 556/415; 556/416; 556/417; 528/41; 528/43; 424/47; 424/60; 424/70.12

(58) Field of Search .................. 424/60, 47, 70.12; 528/41, 43; 556/416, 417, 415, 437

(56) References Cited

U.S. PATENT DOCUMENTS

| | | | |
|---|---|---|---|
| 3,215,719 | 11/1965 | Allen | 260/448.8 |
| 3,859,321 | * 1/1975 | Traver | 260/448.2 |
| 4,374,236 | 2/1983 | Znaiden | 528/26.5 |
| 5,066,419 | 11/1991 | Walley et al. | 252/174.11 |
| 5,077,422 | * 12/1991 | Colas et al. | 556/438 |
| 5,405,983 | * 4/1995 | Fost et al. | 556/405 |
| 5,550,272 | 8/1996 | Lewis et al. | 556/479 |
| 5,827,509 | * 10/1998 | Richard et al. | 424/60 |

FOREIGN PATENT DOCUMENTS

| | | |
|---|---|---|
| 878 497A | * 11/1998 | (EP) . |
| 0 878 497 | 11/1998 | (EP) . |
| 2287955 | * 5/1976 | (FR) . |
| 07150190 | * 6/1995 | (JP) . |
| 07/179328 | 7/1995 | (JP) . |
| 08109263 | * 4/1996 | (JP) . |
| WO 95/04809 | 2/1995 | (WO) . |
| WO 96/19119 | 6/1996 | (WO) . |
| WO 96/28497 | 9/1996 | (WO) . |
| 96/40187 | * 12/1996 | (WO) . |

OTHER PUBLICATIONS

Puyenbroek et al., "Synthesis of siloxanes containing acid-–sensitive side groups", Polymer, vol. 37(5): 847–854, 1996.*

Baron, Derek and Ollis, David W. eds., *Comprehensive Organic Chemistry*, vol. 2, pp. 871–907 (1979).

Hassner and Alexanian, *Tetrahedron Leters.* No. 46, pp. 4475–4478 (1978).

Duhamel, et al., "Unprecedented Route to Enolates from Siyl Enol Ethers . . . " *J. Chem. Soc.* "Perkins Trans. I," 2509 (1993).

Pagington, J.S. *Perfumer & Flavorist*, vol. 11, 49 (Feb./Mar. 1986).

Patent Abstracts of Japan, publication No. 06345873 (1994).

Patent Abstracts of Japan, publication No. 06211874 (1994).

* cited by examiner

*Primary Examiner*—Gary Geist
*Assistant Examiner*—Leigh C. Maier
(74) *Attorney, Agent, or Firm*—Mark E. Waddell; Stephen M. Haracz; Bryan Cave LLP

(57) ABSTRACT

Organosiloxane fragrance precursor compounds having at least one organosiloxane unit of the formula

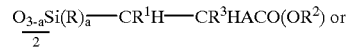 Ia

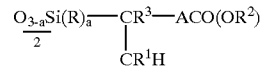 Ib or a mixture thereof and if any other siloxane unit(s) in the said organosiloxanes being present this/these is/are of formula

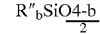

II wherein R represents a substituted or unsubstituted $C_{1-8}$ alkyl group or a substituted or unsubstituted aryl group;

R" represents a hydrogen atom, a monovalent $C_{1-8}$ hydrocarbon group or a monovalent $C_{1-8}$ halogenated hydrocarbon group;

$R^1$ represents a hydrogen atom or a substituted or unsubstituted $C_{1-8}$ alkyl group or a substituted or unsubstituted aryl group or a bond connecting $CR^1$ and $CR^3$;

$R^3$ represents a hydrogen atom or a substituted or unsubstituted $C_{1-8}$ alkyl group or a substituted or unsubstituted aryl group;

„A" represents $(CR^4{}_2)_n$ whereby $R^4$ represents a substituted or unsubstituted $C_{1-8}$ alkyl group or a substituted or unsubstituted aryl group or a hydrogen atom and whereby n is from 0–20 and each $R^4$ is the same or different;

$OR^2$ represents the residue of an olfactive alcohol or of the enol form of an olfactive aldehyde or olfactive ketone;

„a" is 0, 1 or 2; and

„b" is 0, 1, 2 or 3. The compounds can be used in the manufacture of odorant compositions used in the preparation of cosmetic and laundry products.

18 Claims, No Drawings

FRAGRANCE PRECURSOR COMPOUNDS

FIELD OF THE INVENTION

The present invention provides fragrance precursor compounds. In particular, the invention provides a method for the use of several classes of compounds which can act as fragrance precursors in cosmetic products, such as deodorants and antiperspirants. These compounds can also act as fragrance precursors in laundry products such as detergents and fabric softeners. The compounds are normally odorless or nearly so, but upon contacting the skin as, for example, in skin care compositions or in personal care compositions, produce fragrances. The compounds also produce fragrances when used in the presence of lipases, e.g. in laundry products.

BACKGROUND OF THE INVENTION

A principal strategy currently employed in imparting odors to consumer products is the admixing of the fragrance directly into the product. There are however, several drawbacks to this strategy. For example, the fragrance material can be too volatile, resulting in fragrance loss during manufacturing, storage, and use. Many fragrance materials are also unstable over time. This again results in loss of fragrance during storage.

In some cases, fragrances are microencapsulated or treated with cyclodextrins to form inclusion complexes to help decrease volatility and improve stability. However, these methods are for a number of reasons often not successful. In addition, cyclodextrins can be too expensive.

In many consumer products it is desirable for the fragrance to be released slowly over time. Microencapsulation and cyclodextrins have been used to provide slow-release properties, however, they are subject to the same limitations associated with the use of cyclodextrins as stated above.

The Japanese Patent Application No. 07/179 328 discloses sustained release of aromatic compounds which are perfume derivatives for control of perspiration. The compositions perfume when they are gradually decomposed by bacteria usually residing on the body surface, resulting in a long, stable perfuming effect. A preferred derivative is said to contain one or a mixture of phosphoric ester, amino acid and carboxylic derivatives of perfumes. The active fragrancing substance, i.e. an alcohol, an aldehyde or a ketone, is released slowly after laundering a fabric to prolong the fragrancing of the fabric after laundering.

The PCT Application WO 95/04809 discloses the use of esters for scenting fabrics being washed in the presence of a lipase-containing detergent.

The PCT application WO 96/1999119 describes the addition of silicone polymers to perfumes to improve surface residuality of a fragrance. The fragrance is not bound to the polymer.

U.S. Pat. No. 3,215,719 describes silicate esters of essential alcohols where the oxy group RO— of an alcohol is directly bonded to silicone as Si—OR which can be applied to textiles to impart thereto a lasting fragrance.

SUMMARY OF THE INVENTION

The present invention provides compounds which have a low level of odor, or are even odorless, prior to application to the skin, but which release odorant molecules after application to the skin. That is, they provide a delayed release of the fragrance, in particular as they react with microorrganisms present on the skin, i.e. Axilla bacteria. The compounds of the present invention also release odorant molecules when used in the presence of lipase-containing products.

The compounds of the present invention are organosiloxane compounds having at least one unit of the formula

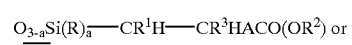   Ia

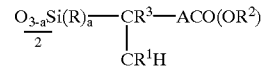   Ib or a mixture thereof. In addition, if any other unit(s) in the siloxanes is/are present this/these unit(s) have the following formula

   II wherein R represents a substituted or unsubstituted $C_{1-8}$ alkyl group or a substituted or unsubstituted aryl group; R" represents a hydrogen atom, a monovalent $C_{1-8}$ hydrocarbon group or a monovalent $C_{1-8}$ halogenated hydrocarbon group; $R^1$ represents a hydrogen atom, a substituted or unsubstituted $C_{1-8}$ alkyl group or a substituted or unsubstituted aryl group or a bond connecting $CR^1$ and $CR^3$; $R^3$ represents a hydrogen atom or a substituted or unsubstituted $C_{1-8}$ alkyl group, or a substituted or unsubstituted aryl group; A represents $(CR^4{}_2)_n$ whereby $R^4$ represents a substituted or unsubstituted $C_{1-8}$ alkyl group, a substituted or unsubstituted aryl group, or a hydrogen atom, n is from 0–20, preferably 1 to 10, and each $R^4$ is the same or different; $OR^2$ represents the residue of an olfactive alcohol or of the enol form of an olfactive aldehyde or olfactive ketone; „a" is 0, 1 or 2; and „b" is 0, 1, 2 or 3.

DETAILED DESCRIPTION OF THE INVENTION

In the general formula of the organosiloxane compounds of the invention, R may be for example methyl, ethyl, butyl or phenyl. R" may be for example alkyl, alkenyl, aryl, alkaryl, aralkyl and halogen substituted alkyl, alkenyl, aryl, alkaryl and aralkyl. Specific examples are methyl, ethyl, vinyl, phenyl and 3,3,3-trifluoropropyl. $R^4$ preferably is a hydrogen atom or methyl. It is preferred that at least 80% of all R and R" groups are methyl groups.

In addition, „a" is preferably 1, while „b" is preferably 2, making either a substantially linear organosiloxane compound or a cyclic diorganosiloxane polymer. However, if the diorganosiloxane is a substantially linear polymer, at least two endblocking units must be present, thus requiring the presence of two units when „a" is 2, two units when the value of „b" is 3, one unit when „a" is 2 and one unit when „b" is 3. Therefore, suitable preferred polymers have either the general formula

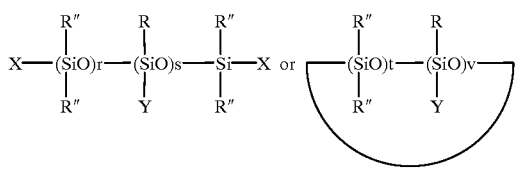

wherein R and R" are as defined above; X denotes a group Y or a group R"; and Y denotes a group of the formula Ia or Ib, „r" is from 0 to 1000; „s" is from 0 to 1000, whereby at least one X denotes Y in the case that „s" =0; „t" has the value of from 0 to 10; and „v" has the value of from 1 to 10. Preferably „v + t" is from 3 to 6. Further embodiments occur when „v + t" is greater than 3, or „v - t" has a value of at least 3.

The organosiloxane compounds of the present invention have at least one unit falling within the general formula Ia or Ib. Suitable organosiloxane compounds include polymeric materials, which may be homopolymers consisting only of such units Ia or Ib or copolymers containing in addition units having the general formula II.

The compounds of formula Ia or Ib are not limited to any particular stereoisomers, all possible stereoisomers as well as racemates are thus included within the scope of formula Ia or Ib.

The units of formula Ia or Ib may be distributed randomly in an organosiloxane copolymer. Units of formula Ia or Ib may be end-blocking units of these polymers or they may be located at both the end of the copolymer and in the chain of the copolymer.

The organosiloxane compounds may vary from freely flowing liquids to highly viscous gum-like materials to resinous solids. Preferred, at least for cosmetic applications, are monomers or liquid, substantially linear, organosiloxane homopolymers and copolymers, most preferably those having a viscosity of from 25 to 500 mm$^2$/s since these are more easily mixed with other ingredients to make cosmetic compositions and they will spread more easily onto the skin.

Suitable examples of alcohols R$^2$OH are primary or secondary alcohols or phenols such as listed in Table 1.

Table 1 amyl alcohol
hexyl alcohol*
2-hexyl alcohol*
heptyl alcohol*
octyl alcohol*
nonyl alcohol*
decyl alcohol*
undecyl alcohol*
lauryl alcohol*
myristic alcohol
3-methyl-but-2-en-1-ol*
3-methyl-1-pentanol
cis-3-hexenol**
cis-4-hexenol**
3,5,5-trimethyl hexanol
3,4,5,6,6-pentamethylheptan-2-ol
citronellol**
geraniol**
oct-1-en-3-ol
2,5,7-trimethyl octan-3-ol
2-cis-3,7-dimethyl-2,6-octadien-1-ol
6-ethyl-3-methyl-5-octen-1-ol*
3,7-dimethyl-oct-3,6-dienol*
3,7-dimethyloctanol*
7-methoxy-3,7-dimethyl-octan-2-ol*
cis-6-nonenol*
5-ethyl-2-nonanol
6,8-dimethyl-2-nonanol*
2,2,8-trimethyl-7 (8)-nonene-3-ol
nona-2,6-dien-1-ol
4-methyl-3-decen-5-ol**
dec-9-en-1-ol
benzylalcohol
2-methyl undecanol
10-undecen-1-ol
1-phenyl ethanol*
2-phenyl ethanol**
2-methyl-3-phenyl-3-propenol
2-phenyl propanol*
3-phenyl propanol*
4-phenyl-2-butanol
2-methyl-5-phenyl pentanol*
2-methyl-4-phenyl-pentanol*
3-methyl-5-phenyl-pentanol*
2-(2-methylphenyl)-ethanol*
4-(1-methylethyl)benzene methanol
4-(4-hydroxyphenyl)butan-2-one*
2-phenoxy ethanol*
4-(1-methylethyl)-2-hydroxy-1-methyl benzene
2-methoxy-4-methyl phenol
4-methyl phenol
anisic alcohol*
p-tolyl alcohol*
cinnamic alcohol**
vanillin*
ethyl vanillin*
eugenol**
isoeugenol**
thymol
anethol*
decahydro 2-naphthalenol
borneol*
cedrenol*
farnesol*
fenchyl alcohol*
menthol*
3,7,11-trimethyl-2,6,10-dodecatrien-1-ol
alpha ionol*
tetrahydro ionol*
2-(1,1-dimethylethyl)cyclohexanol*
3-(1,1-dimethylethyl)cyclohexanol*
4-(1,1-dimethylethyl)cyclohexanol*
4-isopropyl cyclohexanol
6,6-dimethyl-bicyclo[3.3.1]hept-2-ene-2-ethanol
6,6-dimethyl-bicyclo[3.1.1]hept-2-ene-methanol*
p-menth-8-en-3-ol*
3,3,5-trimethyl cyclohexanol
2,4,6-trimethyl-3-cyclohexenyl-methanol*
4-(1-methylethyl)cyclohexyl-methanol*
4-(1,1-dimethylethyl)cyclohexanol
2-(1,1-dimethylethyl)-cyclohexanol
2,2,6-trimethyl-alpha-propyl cyclohexane propanol*
5-(2,2,3-trimethyl-3-cyclopentenyl)-3-methylpentan-2-ol*
3-methyl-5-(2,2,3-trimethylcyclopentyl-3-enyl)pent-4-en-2-ol**
2-ethyl-4(2,2,3-trimethylcyclopentyl-3-enyl)but-2-en-1-ol**
4-(5,5,6-trimethylbicyclo[2.2.1]hept-2-yl)-cyclohexanol*
2-(2-methylpropyl)-4-hydroxy-4-methyl-tetrahydropyran 2-cyclohexyl propanol*
2-(1,1-dimethylethyl)-4-methyl cyclohexanol*
1-(2-tert-butyl-cyclohexyloxy)-2-butanol*
1-(4-isoporpyl-cyclohexyl)-ethanol*.
whereby one asterisk indicates the preferred alcohols and two asterisks indicate the more preferred alcohols.

Suitable examples of aldehydes are listed in Table 2.

Table 2

2,6,10-trimethylundec-9-enal*
undecanal
1,2,3,4,5,6,7,8,-octahydro-8,8-dimethyl-2-napthalenecarboxaldehyde
tridecanal
2-[4-(1-methylethyl)phenyl]-ethanal
1-carboxaldehyde,2,4-dimethyl-cyclohex-3-ene*
4-carboxaldehyde-1,3,5-trimethyl-cyclohex-1-ene*
1-carboxaldehyde-2,4-dimethyl-cyclohex-3-ene*
1-carboxaldehyde-4-(4-hydroxy-4-methylpentyl)-cyclohex-3-ene*
3,5,5-trimethyl-hexanal
heptanal*
2,6-dimethyl-hept-5-eneal*
decanal**
dec-9-enal
dec-4-en-1-al
2-methyldecanal*
undec-10-ene-1-al**
undecanal*
dodecanal**
2-methylundecanal**
tridecanal
octanal**
nonanal*
3,5,5-trimethylhexanal
undec-9-eneal**
2-phenyl-propanal*
4-methyl-phenyl acetaldehyde*
3,7-dimethyl-octanal*
7-hydroxy-3,7-dimethyl-octanal*
2,6-dimethyl-oct-5-ene-1-al
2-(4,-(1-methylethyl)phenyl)-ethanal*
3-(3-isopropylphenyl)-butanal**
2-(3,7-dimethyoct-6-en-oxy)-ethanal
1-carboxaldehyde-4-(4-methyl-3-penten-1-ly)-cyclohex-3-ene*
2,3,5,5,-tetramethyl-hexanal
longifolic aldehyde
2-methyl-4-(2,6,6-trimethylcyclohex-2-en-1-yl)-butanal*
2-methyl-3-(4-tert-butylphenyl)propanal**
4-(1,1-dimethylethyl)-benzenepropanal*
2-[4-(1-methylethyl)phenyl]-propanal
alpha-methyl-1,3-benzodioxole-5-propanal*
3,7-dimethyl-oct-6-en-1-al*
2-methyl-3-(p-isopropylphenyl)-propionaldehyde*
4-(4-hydroxy-4-methylpentyl)-cyclohex-3-en-1-carboxaldehyde**
alpha-methyl-1,3-benzodioxole-5-propanal*
1-carboxaldehyde-4-(1,1-dimethylethyl)-cyclohexane
4-(octahydro-4,7-methano-5H-inden-5-ylidene)-butanal
whereby one asterisk indicates the preferred aldehydes and two asterisks indicate the more preferred aldehydes.

Suitable examples of ketones are listed in Table 3:

Table 3

2-heptyl-cyclopentanone
2,2,6,10-tetrametyltricyclo[5.4.0.0(6,10)]-undecan-4-one
benzylacetone*
carvone*
1,2,3,5,6,7-hexahydrol,1,2,3,3,-pentamentyl-4H-inden-4-one*
methyl heptenone*
dimethyl octenone*
2-(butan-2-yl)-cyclohexanone*
2-hexyl-cyclopent-2-en-1-one*
2-(1-methylethyl)-5-methyl-cyclohexanone*
2-(2-methylethyl)-5-methyl-cyclohexanone*
3-methyl-cyclopentadecanone
4-tert-pentyl-cyclohexanone*
2-oxo-1-pentyl-cyclopentaneacetic acid methyl ester**
1-(1,2,3,4,5,6,7,8-octahydro-2,3,8,8-tetramethyl-2-naphthalenyl)-ethanone*
3-methyl-5-propyl-cyclohex-2-en-1-one*
whereby one asterisk indicates the preferred ketones and the two asterisks indicate the more preferred ketone.

It is a matter of course that it is not possible to give complete lists of the odoriferous alcohols or aldehydes or ketones which are liberated as a result of the desired cleavage of the compounds of formula Ia or Ib, e.g. by bacteria, in particular axilla bacteria, or lipases and which alcohols, aldehydes and ketones are then capable of imparting agreeable odors. The skilled artisan is, however, quite aware of those alcohols, aldehydes and ketones which provide a positive contribution to the fragrance compositions.

The compounds of formula Ia and/or Ib are preferably used as sustained release odorants but also to mask or attenuate undesirable odors or to provide additional odors not initially present in consumer products, i.e. cosmetic products destined for application to human skin such as underarm deodorants or antiperspirants or other deodorants contacting the body, or in hand lotions, baby powders, baby lotions, ointments, foot products, facial cleansers, body wipes, facial make-up, colognes, after-shave lotions, shaving creams, etc. Additional applications include laundry detergents, fabric softeners, fabric softener sheets, automatic dishwasher detergents, and other lipase-containing consumer products.

The compounds of formula Ia and/or Ib are virtually odorless under normal temperature, i.e. at about 10–50 degrees Celsius, and at atmospheric conditions and about 20 to 100% relative humidity. However, when applied to the body or when used in an application in the presence of lipases, they undergo a transformation in which the fragrant alcohol or aldehyde or ketone is released.

As said before, the compounds of formula Ia and/or Ib, upon cleavage, provide alcohols, aldehydes, and ketones having organoleptic properties and therefore permit the development of methods useful in presenting or enhancing the odor of consumer products. These compounds may be used individually in an amount effective to enhance the characteristic odor of a material. More commonly, however, the compounds are mixed with other fragrance components in an amount sufficient to provide the desired odor characteristics.

The amount required to produce the desired, overall effect varies depending upon the particular compound(s) of formula Ia and/or Ib chosen, the product in which it will be used, and the particular effect desired.

For example, depending upon the selection and concentration of the compound chosen, when a compound of formula Ia or Ib is added either singularly or as a mixture, e.g. to a deodorant or laundry product composition at levels ranging from about 0.1 to about 10% by weight, or most preferred about 0.25 to about 4% by weight, an odorant, i.e. an odoriferous alcohol or aldehyde or ketone, in an organoleptically effective amount is released. This newly formed odorant produces or serves to enhance the odor of the fragrance.

The compounds of formula Ia and/or Ib can accordingly be used in the manufacture of odorant compositions used in the preparation of cosmetic and laundry products, e.g. deodorants, antiperspirants, laundry detergents, fabric softeners, and as is evident from the above compilation, a broad range of known odorants or odorant mixtures can be used. In the manufacture of such compositions the known odorants or odorant mixtures set forth above can be used according to methods known to a person skilled in the art, normally a perfumer, or as described, e.g. in W. A. Poucher, Perfumes, Cosmetics, Soaps, 2, 7th Edition, Chapman and Hall, London 1974.

The compounds of formula Ia or Ib can be prepared by using standard methods known to a person skilled in the art. For example the method disclosed by U.S. Pat. No. 5,550,272 can be used. The organosiloxane compounds of the present invention can be prepared by the reaction of an organosiloxane having at least one unit of the general formula

with an unsaturated ester or enol ester having a radical $OR^2$ of a fragrant alcohol, aldehyde or ketone, a compound of the general formula

Esters of the general formula III may be prepared from the corresponding carboxylic acids and alcohols by standard methods known per se. (For example see, Comprehensive Organic Chemistry, Derek Barton and W. David Ollis, eds. Vol. 2, 1979, pp.871–907). For example, esters are formed by the acid catalyzed reaction between a carboxylic acid and an alcohol. During the condensation, water is usually removed.

Either protic or Lewis acids may be used. Some acids which may be used are p-toluensulfonic acid, sulfuric acid, and pyridinium p-toluenesulfonate. A variety of inert solvents may be used such as toluene, xylene, cyclohexane, and hexane.

In another example, a carboxylic acid and an alcohol react to form an ester when treated with N,N'-dicyclohexycarbodiimide and 4-pyrrolidinopyridine. (For example see, the procedure of Hassner and Alexanian in Tetrahedron Letters 4475, (1978)).

Enol esters of the general formula III may be prepared using the procedure of J. Chem. Soc., Perkin Trans. I, 2509 (1993).

The preferred preparation of organosiloxane compounds of the type Ia or Ib comprises reacting a compound of the general formula III and an organosiloxane compound having at least one unit of the general formula IV, any other units present being those represented by the general formula II.

The reaction is preferably carried out employing stoichiometric proportions of compounds III and IV or a slight stoichiometric excess of compound III. However, a stoichiometric deficiency of compound III can be employed if residual silicon-bonded hydrogen is desired in the product.

The reaction between compounds III and IV may be carried out employing known procedures for the addition of silicon-bonded hydrogen atoms to groups containing aliphatic unsaturation. Thus, such reactions are generally catalyzed by a platinum group metal or a compound or complex of such a metal. Examples of catalysts which may be employed in the reaction between compounds III and IV are platinum on carbon, chloroplatinic acid, platinum acetyl acetonate, complexes of platinum compounds with unsaturated compounds, e.g. olefins and vinyl siloxanes, complexes of rhodium and palladium compounds and complexes of platinum compounds supported on inorganic substrates. The addition reaction may be performed at reduced, atmospheric or increased pressure. It is generally preferred to employ a solvent, e.g. toluene or xylene in the reaction mixture although the presence of a solvent is not essential. It is also preferred to carry out the reaction at elevated reaction temperatures e.g. ranging from room temperature up to the reflux temperature of the reaction mixture.

EXAMPLES

The present invention is described further in the following examples which are presented solely for the non-limiting purpose of further illustrating the invention.

Example 1

Pent-4-enoic Acid Phenethyl Ester

A solution of 29.3 g 4-pentenoic acid, 37.0 g phenylethyl alcohol, 1.0 g p-toluenesulfonic acid and 300 ml cyclohexane was refluxed in a flask equipped with a Dean-Stark trap for 4 hours. The reaction mixture was cooled, diluted with ether, washed with aqueous $NaHCO_3$ and brine. The organic phase was dried, filtered and evaporated to dryness. The resulting liquid was distilled to yield 42.6 g of a colorless liquid.

NMR ($CDCl_3$) δ 7.39–7.20 (m, 5 H), 5.91–5.68 (m, 1H), 5.12–4.93 (m, 2H), 4.30 (t, 2H), 2.94 (t, 2H), 2.48–2.29 (m, 4H).

According to the same procedure, pent-4-enoic acid 3,7-dimethyl-octyl ester was prepared from tetrahydrogeraniol and 4-pentenoic acid.

According to the same procedure, undec-10-enoic acid phenethyl ester was prepared from phenylethyl alcohol and 10-undecenoic acid.

Example 2

Pent-4-enoic Acid 3,7-dimethyl-octa-2,6-dienyl Ester

A solution of 24.5 g 4-pentenoic acid, 40.1 g geraniol, 52.1 g N,N'-dicyclohexylcarbodiimide, 2.8 g 4-pyrrolidinopyridine, and 400 ml dichloromethane was stirred at room temperature for 24 hours. The reaction was filtered, the solid washed with ether and the combined organic layers washed with water, aqueous HCl, aqueous $NaHCO_3$, and brine. The organic phase was dried and evaporated to dryness. The residue was distilled to yield 33.6 g of a colorless liquid.

NMR ($CDCl_3$) δ 5.96–5.72 (m, 1H), 5.40–5.40 (m, 1H), 5.16–4.93 (m, 3H), 4.67–4.54 (m, 2H), 2.47–2.38 (m, 4H), 2.20–1.98 (m, 4H), 1.72 (s, 3H), 1.70 (s, 3H), 1.60 (s, 3H).

According to the same procedure, pent-4-enoic acid 3,7-dimethyl-oct-6-enyl ester was prepared from citronellol and 4-pentenoic acid.

According to the same procedure, undec-10-enoic acid 3,7-dimethyl-oct-2,6-dienyl ester was prepared from geraniol and 10-undecenoic acid.

Example 3

5-(1,1,3,3,3-Pentamethyl-disiloxanyl)-pentanoic Acid Phenethyl Ester

A solution of 5.1 g pent-4-enoic acid phenethyl ester, 1.0 g 5% Pt/C, 3.8 g pentamethyldisiloxane, and 50 ml toluene was stirred at room temperature under nitrogen for 24 hours. The solution was filtered through Celite and evaporated to dryness to yield 8.6 g of a colorless oil.

NMR (CDCl$_3$) δ 7.32–7.13 (m, 5H), 4.21 (t, 2H), 2.89 (t, 2H), 2.31–2.19 (m, 2H), 1.67–1.50 (m, 2H), 1.37–1.19 (m, 2H), 0.5–0.4 (m, 2H), 0.02 (s, 15H).

According to the same procedure, 5-(1,1,3,3,3-pentamethyl-disiloxanyl)-pentanoic acid 3,7-dimethyl-octyl ester was prepared from pent-4-enoic acid 3,7-dimethyl-octyl ester and pentamethyldisiloxane.

According to the same procedure, 11-(1,1,3,3,3-pentamethyl-disiloxanyl)-undecanoic acid phenethyl ester was prepared from undec-10-enoic acid phenethyl ester and pentamethyldisiloxane.

According to the same procedure, a polymer containing units of the general structures Ia and Ib and II was prepared from pent-4-enoic acid phenethyl ester and a hydrosiloxane of the general formula IV, whereby the structure type Ia is dominating.

According to the same procedure, a polymer containing units of the general structures Ia and Ib and II was prepared from pent-4-enoic acid 3,7-dimethyl-octyl ester and a hydrosiloxane of the general formula IV, whereby the structure type Ia is dominating.

According to the same procedure, a polymer containing units of the general structures Ia and Ib and II was prepared from undec-10-enoic acid phenethyl ester and a hydrosiloxane of the general formula IV, whereby the structure type Ia is dominating.

According to the same procedure, 5-{2,4,6,8-tetramethyl-4,6,8-tris-(4-phenethyloxycarbonyl-butyl)-[1,3,5,7,2,4,6,8]tetroxatetrasilocan-2-yl}-pentanoic acid phenethyl ester was prepared from pent-4-enoic acid phenethyl ester and 2,4,6,8-tetramethylcyclotetrasiloxane.

Example 4

5-(1,1,3,3,3-Pentamethyl-disiloxanyl)-pentanoic Acid 3,7-dimethyl-oct-6-enyl Ester A solution of 6.0 g pent-4-enoic acid 3,7-dimethyl-oct-6-enyl ester, 1.0 g Pt/C, 3.8 g pentamethyldisiloxane, 0.05 g 2,2,6,6-tetramethyl-1-piperidinyloxy, free radical, and 50 ml toluene was stirred at room temperature for 24 hours. The solution was filtered through Celite and evaporated to dryness to yield 9.8 g of an oil.

NMR (CDCl$_3$) δ 5.09–4.96 (m, 1H), 4.09–3.97 (m, 2H), 2.25–2.18 (m, 2H), 2.17–1.81 (m, 2H), 1.64 (s, 3H), 1.55 (s, 3H), 1.60–1.05 (m, 9H), 0.84 (d, 3H), 0.53–0.42 (m, 2H), 0.02 (s, 15H).

According to the same procedure, 5-(1,1,3,3,3-pentamethyl-disiloxanyl)-pentanoic acid 3,7-dimethyl-octa-2,6-dienyl ester was prepared from pent-4-enoic acid 3,7-dimethyl-octa-2,6-dienyl ester and pentamethyldisiloxane.

According to the same procedure, 11-(1,1,3,3,3-pentamethyl-disiloxanyl)-undecanoic acid 3,7-dimethyl-oct-6-enyl ester was prepared from undec-10-enoic acid 3,7-dimethyl-oct-6-enyl ester and pentamethyldisiloxane.

According to the same procedure, except that the reaction was heated at 50° C., a polymer containing the general structures Ia and Ib and II was prepared from pent-4-enoic acid 3,7-dimethyl-oct-6-enyl ester and a hydrosiloxane of the general formula IV, whereby the structure type Ia is dominating.

According to the same procedure, 11-(1,1,3,3,3-pentamethyl-disiloxanyl)-undecanoic acid 3,7-dimethyl-octa-2,6-dienyl ester was prepared from undec-10-enoic acid 3,7-dimethyl-octa-2,6-dienyl ester and pentamethyldisiloxane.

According to the same procedure, 5-{4,6,8-tris-[4-(3,7-dimethyl-oct-6-enyloxycarbonyl)-butyl]-2,4,6,8-tetramethyl-[1,3,5,7,2,4,6,8]tetroxatetra-silocan-2-yl}-pentanoic acid 3,7-dimethyl-oct-6-enyl ester was prepared from pent-4-enoic acid 3,7-dimethyl-oct-6-enyl ester and 2,4,6,8-tetramethylcyclotetrasiloxane.

According to the same procedure, 5-{3-[4-(3,7-dimethyl-oct-6-enyloxycarbonyl)-butyl]-1,1,3,3-tetramethyl-disiloxanyl}-pentanoic acid 3,7-dimethyl-oct-6-enyl ester was prepared from pent-4-enoic acid 3,7-dimethyl-oct-6-enyl ester and tetramethyldisiloxane.

Example 5

E,Z-Acetic acid 3-(4-tert-butyl-phenyl)-2-methyl-propenyl Ester

A solution of 200 g 2-methyl-3-(4-tert-butylphenyl) propanal, 280 ml triethylamine and 13.4 g sodium acetate in 800 ml of acetic anhydride was stirred at 120° C. for 5.5 hours. Then the solution was cooled, water was added and the water phase was extracted with hexane. The organic phase was washed with 2N NaOH and water to neutrality, dried and evaporated to dryness. The residue was distilled to yield 185 g of a colourless liquid.

NMR (CDCl$_3$) δ 7.35–6.97 (m, 5 H), 3.43+3.21 (s, 2 H, E/Z), 2.13 (s, 3 H), 1.60 (s, 3 H), 1.30 (s, 9H).

According to the same procedure, acetic acid 3-(3-isopropyl-phenyl)-but-1-enyl ester was prepared from 3-(3-isopropylphenyl)-butanal and acetic anhydride.

Example 6

E,Z-Undec-10-enoic Acid 3-(4-tert-butyl-phenyl)-2-methyl-propenyl Ester

To a solution of 40.0 g acetic acid 3-(4-tert-butyl-phenyl)-2-methyl-propenyl ester in 200 ml THF a solution of 24.3 g potassium t.butoxide in 200 ml THF was dropped in at −70° C. After 90 min. at −70° C. 36.5 g 10-undecenoylchloride were dropped in at the same temperature. After 4 hours 250 ml of saturated NaHCO$_3$ were dropped in and the solution was diluted with ether, washed neutral with water, dried and evaporated to dryness. The residue was thin-layer-distilled to yield 35.8 g colourless liquid.

NMR (CDCl$_3$) δ 7.39–6.96 (m, 5 H), 5.93–5.68 (m, 1 H), 5.06–4.87 (m, 2 H), 3.46+3.18 (s, 2 H, E/Z), 2.39 (t, 2 H), 2.12–1.93 (m, 2 H), 1.78–1.52 (m, 5 H), 1.48–1.12 (m,19 H).

According to the same procedure, except that the reaction was stirred for 40 hours, E/Z-11-(1,1,3,3,3-Pentamethyl-disiloxanyl)-undecanoic acid 3-(4-tert-butyl-phenyl)-2-methyl-propenyl ester was prepared from undec-10-enoic acid 3-(4-tert-butyl-phenyl)-2-methyl-propenyl ester and pentamethyldisiloxane.

According to the same procedure, undec-10-enoic acid 3-(3-isoproyl-phenyl)-but-1-enyl ester was prepared from acetic acid 3-(3-isopropyl-phenyl)-but-1-enyl ester and 10-undecenoyl chloride.

According to the same procedure, 11-(1,1,3,3,3-pentamethyl-disiloxanyl)-undecanoic acid 3-(3-isopropyl-phenyl)-but-1-enyl ester was prepared from undec-10-enoic acid 3-(3-isoproyl-phenyl)-but-1-enyl ester and pentamethyl disiloxane.

Example 7

Test cloth was washed with a lipase-containing detergent to which one or more delayed release fragrances had been added. Headspace analysis of the wet and dry laundry indicated the presence of the fragrant alcohols. The alcohol level was higher than when the test cloth was washed with a lipase-containing detergent to which one or more fragrant alcohols were added.

Example 8

Test cloth was washed with a lipase-containing detergent and then a fabric softener, containing one or more delayed release fragrances, was added to the rinse cycle. Headspace analysis of the wet and dry laundry indicated the presence of the fragrant alcohols. The alcohol level was higher than when the test cloth was washed with a lipase-containing detergent and then a fabric softener, containing one or more fragrant alcohols, was added to the rinse cycle.

Example 9

Axilla bacteria cultures containing 0.1% precursor I were incubated for 20 hours at 30° C. After filtration from the cells, the presence of the parent alcohol was in each case detected by headspace-GC techniques and/or the majority of an 18 member panel.

The same tests were carried out with inactivated cultures (85°/20 min). The odor of the parent alcohols could not be detected after incubation, excluding therefore a hydrolysis by the medium or the culture.

Example 10

The following set forth examples for the use of the delayed release fragrances of the present invention in various products. The methods of forming the following compositions are well known to those skilled in the art. All formulations may contain additional ingredients known to those skilled in the art, e.g. colorants, opacifiers, buffers, antioxidants, vitamins, emulsifiers, UV absorbers, silicones and the like. All products can also be buffered to the desired pH. All values are % w/w.

| Deo-colognes | | | | |
|---|---|---|---|---|
| Delayed Release Fragrances | 0.5 | 1.5 | 2.5 | 6.0 |
| Fragrance | 0.5 | 1.5 | 2.5 | 6.0 |
| Triclosan (Ciba Geigy) | 1.0 | — | 0.75 | 1.0 |
| Alcohol to | 100 | 100 | 100 | 100 |

| Deo-Sticks | |
|---|---|
| Antiperspirant | |
| Ethylene Glycol Monostearate | 7.0 |
| Shea butter | 3.0 |
| NEOBEE 1053 (PVO International) | 12.0 |
| GENEROL 122 (Henkel) | 5.0 |
| KESSCOWAX B (Akzo) | 17.0 |
| DIMETHICONE Dow Corning 345 | 35.0 |
| Aluminum Sesquichlorhydrate | 20.0 |
| Delayed Release Fragrances | 0.5 |
| Fragrance | 0.5 |
| Antiperspirant | |
| Steary Alcohol | 17.0 |
| Castor Wax | 3.0 |
| Talc | 5.0 |
| Aluminum Zirconium Tetrachlorhydrate | 20.0 |
| Delayed Release Fragrances | 1.0 |
| Fragrance | 1.0 |
| DIMETHICONE Dow 245 to | 100.0 |
| Clear Deodorant Stick | |
| WITCONOL APM | 43.0 |
| Propylene Glycol | 20.0 |
| Alcohol 39C | 20.0 |
| Demin water | 7.0 |
| MONAMID 150ADD | 5.0 |
| MILLITHIX 925 | 2.0 |
| OTTASEPT EXTRA | 0.5 |
| Delayed Release Fragrances | 0.75 |
| Fragrance | 0.75 |
| Deodorant Stick | |
| Propylene Glycol | 69.0 |
| Demin Water | 21.8 |
| Triclosan | 0.2 |
| Sodium Stearate | 8.0 |
| Delayed Release Fragrances | 0.5 |
| Fragrance | 0.5 |
| Alcohol free Deodorant Stick | |
| PPG-3 Myristyl Ether (WITCONOL APM) | 36.0 |
| Propylene Glycol | 36.0 |
| Demin Water | 19.0 |
| Triclosan | 0.25 |
| Sodium Stearate | 7.75 |
| Delayed Release Fragrances | 0.5 |
| Fragrance | 0.5 |
| Antiperspirant Aerosol | |
| Absolute Ethanol | 15.0 |
| Zirconium Aluminum tetrachlorhydrate | 5.0 |
| BENTONE 38 | 1.5 |
| Delayed Release Fragrances | 0.75 |
| Fragrance | 0.75 |
| S-31 Hydocarbon propellant to | 100.0 |
| Antiperspirant Pump | |
| Demin water | 57.5 |
| Aluminum Sesquichlorhydrate | 20.0 |
| TRITON ® X-102 | 2.0 |
| (Union Carbide) (octoxynol-13) | |
| Dimethyl Isosorbide (ICI) | 20.0 |
| Delayed Release Fragrances | 0.25 |
| Fragrance | 0.25 |
| Roll-On | |
| DIMETHICONE DC 354 (Dow Corning) | 69.0 |
| BENZONE 38 | 10.0 |
| REZAL ® 36 GP (Reheis Chem. Co.) | 20.0 |
| (aluminium zirconium tetrachlorohydrexglycine) | |
| Delayed Release Fragrances | 0.5 |
| Fragrance | 0.5 |

In the above, the following components were used:

| | |
|---|---|
| Triclosan | 5-chloro-2-(2,4-dichlorophenoxy)phenol |
| NEOBEE 1053 | glycerol tricaprate/caprylate |
| GENEROL 122 | soya sterol |
| KESSCOWAX B | cetyl alcohol and glycol polymer |
| WITCONOL APM | polypropylene glycol-3 myristyl ether |
| MONAMID 150 ADD | cocoamide diethanolamine |
| MILLITHIX 925 | dibenzylidene sorbitol |

-continued

| | |
|---|---|
| OTTASEPT EXTRA | quaternium 18 hectorite |
| BENTONE 38 | quaternium 18 hectorite |
| TRITON X-102 | octoxynol-13 |
| DIMETHICONE DC 354 | mixture of fully methylated linear siloxanepolymers end-blocked with trimethylsiloxy units |
| REZAL 36 GP | Aluminium zirconium tetrachlorohydrexglycine |

While the invention has been illustrated and described with respect to the illustrative embodiments and modes of practice, it will be apparent to those skilled in the art that various modifications and improvements may be made without departing from the scope and spirit of the invention. Accordingly, the invention is not to be limited by the illustrative embodiments and modes of practice.

We claim:

1. A fragrance precursor compound of the general formula Ia or Ib:

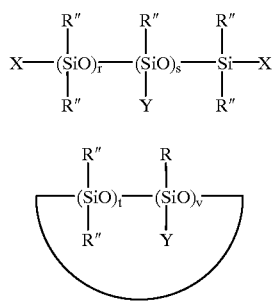

wherein X represents a group Y or a group R",
Y represents a group of the formula:

$-CR^1H-CR^3HACO(OR^2)$;

A represents $(CR^4{}_2)_n$ wherein $R^4$ represents a substituted or unsubstituted $C_{1-8}$ alkyl group or a substituted or unsubstituted phenyl group or a hydrogen atom and whereby n is from 0–20 and each $R^4$ is the same or different;

R represents a substituted or unsubstituted $C_{1-8}$ alkyl group or a substituted or unsubstituted phenyl group;

R" represents a hydrogen atom or a monovalent $C_{1-8}$ hydrocarbon group;

$R^1$ represents a hydrogen atom or a substituted or unsubstituted $C_{1-8}$ alkyl group or a substituted or unsubstituted phenyl group or a bond connecting $CR^1$ and $CR^3$;

$R^3$ represents a hydrogen atom or a substituted or unsubstituted $C_{1-8}$ alkyl group or a substituted or unsubstituted phenyl group;

$OR^2$ represents the residue of an olfactory alcohol or of the enol form of an olfactory aldehyde or olfactory ketone;

wherein "r" is from 0 to 250; "s" is from 0 to 20, and wherein at least one X denotes Y in the case that "s"=0; "t" is from 0 to 10; and "v" is from 1 to 10.

2. A compound according to claim 1 wherein „t+v" is from 3 to 6.

3. A compound according to claim 1 wherein if „v+t" is greater than 3, „v-t" is at least 3.

4. A compound according to claim 1 having the formula

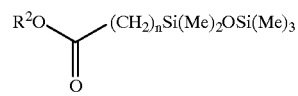

5. A compound according to claim 1 having the formula

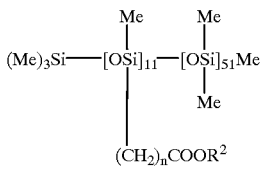

6. A compound according to claim 1 wherein „n" of „A" is from 1 to 10.

7. A cosmetic composition comprising at least one of the compounds of claim 1 wherein the viscosity is from about 25 mm²/s to about 500 mm²/s.

8. A compound according to claim 1 wherein $OR^2$ is a radical derived from a fragrant alcohol selected from amyl alcohol
hexyl alcohol
2-hexyl alcohol
heptyl alcohol
octyl alcohol
nonyl alcohol
decyl alcohol
undecyl alcohol
lauryl alcohol
myristic alcohol
3-methyl-but-2-en-1-ol
3-methyl-1-pentanol
cis-3-hexenol
cis-4-hexenol
3,5,5-trimethyl hexanol
3,4,5,6,6-pentamethylheptan-2-ol
citronellol
geraniol
oct-1-en-3-ol
2,5,7-trimethyl octan-3-ol
2-cis-3,7-dimethyl-2,6-octadien-1-ol
6-ethyl-3-methyl-5-octen-1-ol
3,7-dimethyl-oct-3,6-dienol
3,7-dimethyloctanol
7-methoxy-3,7-dimethyl-octan-2-ol
cis-6-nonenol
5-ethyl-2-nonanol
6,8-dimethyl-2-nonanol
2,2,8-trimethyl-7 (8)-nonene-3-ol
nona-2,6-dien-1-ol
4-methyl-3-decen-5-ol
dec-9-en-1-ol
benzylalcohol
2-methyl undecanol
10-undecen-1-ol
1-phenyl ethanol 2-phenyl ethanol
2-methyl-3-phenyl-3-propenol
2-phenyl propanol
3-phenyl propanol
4-phenyl-2-butanol
2-methyl-5-phenyl pentanol
2-methyl-4-phenyl-pentanol
3-methyl-5-phenyl-pentanol
2-(2-methylphenyl)-ethanol
4-(1-methylethyl)benzene methanol
4-(4-hydroxyphenyl)butan-2-one
2-phenoxy ethanol
4-(1-methylethyl)-2-hydroxy-1-methyl benzene
2-methoxy-4-methyl phenol
4-methyl phenol
anisic alcohol
p-tolyl alcohol
cinnamic alcohol
vanillin
ethyl vanillin
eugenol
isoeugenol
thymol
anethol
decahydro 2-naphthalenol
borneol
cedrenol
farnesol
fenchyl alcohol
menthol
3,7,11-trimethyl-2,6,10-dodecatrien-1-ol
alpha ionol
tetrahydro ionol
2-(1,1-dimethylethyl)cyclohexanol
3-(1,1-dimethylethyl)cyclohexanol
4-(1,1-dimethylethyl)cyclohexanol
4-isopropyl cyclohexanol
6,6-dimethyl-bicyclo[3.3.1]hept-2-ene-2-ethanol
6,6-dimethyl-bicyclo[3.1.1]hept-2-ene-methanol
p-menth-8-en-3-ol
3,3,5-trimethyl cyclohexanol
2,4,6-trimethyl-3-cyclohexenyl-methanol
4-(1-methylethyl)cyclohexyl-methanol
4-(1,1-dimethylethyl)cyclohexanol
2-(1,1-dimethylethyl)-cyclohexanol
2,2,6-trimethyl-alpha-propyl cyclohexane propanol
5-(2,2,3-trimethyl-3-cyclopentenyl)-3-methylpentan-2-ol
3-methyl-5-(2,2,3-trimethylcyclopentyl-3-enyl)pent-4-en-2-ol
2-ethyl-4(2,2,3-trimethylcyclopentyl-3-enyl)but-2-en-1-ol
4-(5,5,6-trimethylbicyclo[2.2.1]hept-2-yl)-cyclohexanol
2-(2-methylpropyl)-4-hydroxy-4-methyl-tetrahydropyran
2-cyclohexyl propanol
2-(1,1-dimethylethyl)-4-methyl cyclohexanol
1-(2-tert-butyl-cyclohexyloxy)-2-butanol, and
1-(4-isoporpyl-cyclohexyl)-ethanol.

9. A compound according to claim 8 wherein the radical is derived from a fragrant alcohol selected from the group consisting of hexyl alcohol, 2-hexyl alcohol, heptyl alcohol, octyl alcohol, nonyl alcohol, decyl alcohol, undecyl alcohol, lauryl alcohol, 3-methyl-but-2-en-1-ol, cis-3-hexenol, cis-4-hexenol, 3,4,5,6,6-pentamethylheptan-2-ol, citronellol, geraniol, 6-ethyl-3-methyl-5-octen-1-ol, 3,7-dimethyl-oct-3,6-dienol, 3,7-dimethyloctanol, 7-methoxy-3,7-dimethyl-octan-2-ol, cis-6-nonenol, 6,8-dimethyl-2-nonanol, 4-methyl-3-decen-5-ol, 1-phenyl ethanol, 2-phenyl ethanol, 2-phenyl propanol, 3-phenyl propanol, 2-methyl-5-phenyl pentanol, 2-methyl-4-phenyl-pentanol, 3-methyl-5-phenyl-pentanol, 2-(2-methylphenyl)-ethanol, 4-(4-hydroxyphenyl) butan-2-one, 2-phenoxy ethanol, anisic alcohol, p-tolyl alcohol, cinnamic alcohol, vanillin, ethyl vanillin, eugenol, isoeugenol, anethol, borneol, cedrenol, farnesol, fenchyl alcohol, menthol, alpha ionol, tetrahydro ionol, 2-(1,1-dimethylethyl)cyclohexanol, 3-(1,1-dimethylethyl) cyclohexanol, 4-(1,1-dimethylethyl)cyclohexanol, 6,6-dimethyl-bicyclo[3.1.1]hept-2-ene-methanol, p-menth-8-en-3-ol, 2,4,6-trimethyl-3-cyclohexenyl-methanol, 4-(1-methylethyl)cyclohexyl-methanol, 2,2,6-trimethyl-alpha-propyl cyclohexane propanol, 5-(2,2,3-trimethyl-3-cyclopentenyl)-3-methylpentan-2-ol, 3-methyl-5-(2,2,3-trimethylcyclopentyl-3-enyl)pent-4-en-2-ol, 2-ethyl-4-(2,2,3-trimethylcyclopentyl-3-enyl)but-2-en-1-ol, 4-(5,5,6-trimethylbicyclo[2.2.1]hept-2-yl)-cyclohexanol, 2-(2-methylpropyl)-4-hydroxy-4-methyl-tetrahydropyran, 2-cyclohexyl propanol, 2-(1,1-dimethylethyl)-4-methyl cyclohexanol, 1-(2-tert-butyl-cyclohexyloxy)-2-butanol, and 1-(4-isoporpyl-cyclohexyl)-ethanol.

10. A compound according to claim 9 wherein the radical is derived from a fragrant alcohol selected from the group consisting of citronellol, geraniol, cis-3-hexenol, 4-methyl-3-decen-5-ol, 2-phenyl ethanol, iso eugenol, 3-methyl-5-(2,2,3-trimethylcyclopentyl-3-enyl)pent-4-en-2-ol, 2-ethyl-4-(2,2,3-trimethylcyclopentyl-3-enyl)but-2-en-2-ol, cinnamic alcohol and eugenol.

11. A compound according to claim 1 having a formula selected from the group consisting of 5-(1,1,3,3,3-penta methyl-disiloxanyl)-pentanoic acid phenethyl ester, 5-(1,1,3,3,3-penta methyl-disiloxanyl pentanoic acid 3,7-dimethyl-oct-6-enyl-ester and E,Z-undec-10-enoic acid 3-(4-ter-butyl-phenyl)2-methyl-propenyl ester.

12. A compound according to claim 1, having the formula

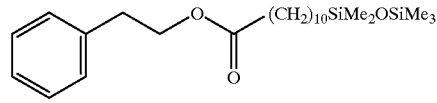

13. A composition for cosmetic application to the human skin, laundry products, detergents or fabric softeners comprising at least one of the compounds according to claim 1.

14. A cosmetic product, a laundry product, a detergent or a fabric softener comprising at least one of the compounds according to claim 1.

15. A process for prolonging the effect of diffusion of the characteristic odor of an odoriferous alcohol, aldehyde or ketone comprising applying at least one of the compounds of claim 1 to a recipient selected from the group consisting of human skin, laundry products, detergents or fabric softeners.

16. A method of suppressing human body malodor by means of applying a composition of claim 13 to the human skin.-

17. A method of suppressing human body malodor comprising applying a composition of claim 14 to the human skin.

18. A process for preparing a product comprising adding at least one of the compounds of claim 1 as a fragrance precursor to a cosmetic composition, or cosmetic product, laundry product, detergent or fabric softener.

$$O_{\underline{3-a}\over 2}Si(R)_{\underline{a}} - \underset{\underset{CR^1H}{|}}{CR^3} - ACO(OR^2)$$

* * * * *

UNITED STATES PATENT AND TRADEMARK OFFICE
CERTIFICATE OF CORRECTION

PATENT NO. : 6,262,287 B1
DATED : July 17, 2001
INVENTOR(S) : Denise Anderson et al.

It is certified that error appears in the above-identified patent and that said Letters Patent is hereby corrected as shown below:

Column 18,
Line 1, please delete the chemical structure.

Signed and Sealed this

Twenty-sixth Day of March, 2002

Attest:

JAMES E. ROGAN
*Attesting Officer*     *Director of the United States Patent and Trademark Office*